United States Patent
Cristiano et al.

(10) Patent No.: US 9,556,219 B2
(45) Date of Patent: Jan. 31, 2017

(54) PROCEDURE FOR THE PREPARATION OF ABIRATERONE ACETATE AND INTERMEDIATES THEREOF

(71) Applicant: Olon S.P.A., Rodano (Mi) (IT)

(72) Inventors: Tania Cristiano, Milan (IT); Marco Alpegiani, Rodano (IT)

(73) Assignee: OLON S.P.A., Rodano (IT)

(*) Notice: Subject to any disclaimer, the term of this patent is extended or adjusted under 35 U.S.C. 154(b) by 0 days.

(21) Appl. No.: 15/114,089

(22) PCT Filed: Jan. 27, 2015

(86) PCT No.: PCT/IB2015/050613
§ 371 (c)(1),
(2) Date: Jul. 26, 2016

(87) PCT Pub. No.: WO2015/114518
PCT Pub. Date: Aug. 6, 2015

(65) Prior Publication Data
US 2016/0347786 A1    Dec. 1, 2016

(30) Foreign Application Priority Data

Jan. 28, 2014 (IT) ............................. MI2014A0111

(51) Int. Cl.
*C07J 43/00* (2006.01)
*C07J 31/00* (2006.01)

(52) U.S. Cl.
CPC ............. *C07J 43/003* (2013.01); *C07J 31/006* (2013.01)

(58) Field of Classification Search
CPC ................................ C07J 43/003; C07J 31/006
See application file for complete search history.

(56) References Cited

FOREIGN PATENT DOCUMENTS

| WO | 9320097 A1 | 10/1993 |
| WO | 2006021777 A1 | 3/2006 |
| WO | 2013053691 A1 | 4/2013 |

OTHER PUBLICATIONS

Arcadi, et al.: "Palladium-catalysed coupling of aryl and viny triflates or halides with 2-ethynylaniline: an efficient route to functionalized 2-substituted indoles", Tetrahedron Letter, Pergamon, GB vol. 30, No. 19, Jan. 1, 1989, pp. 2581-2584.
International Search Report of PCT/IB2015/050613 of Sep. 21, 2015.
Invitation to pay additional fees for PCT/IB2015/050613 of Apr. 21, 2015.
Search Report and Written Opinion of PCT/IB2015/050613 of Sep. 21, 2015.

*Primary Examiner* — Kahsay Habte
(74) *Attorney, Agent, or Firm* — Silvia Salvadori, P.C.; Silvia Salvadori

(57) ABSTRACT

Disclosed is a process for the preparation of abiraterone and abiraterone acetate with high yields and purity. A key element of the method is the isolation of a crystalline intermediate that makes the process particularly suitable for implementation on an industrial scale. There is also provided a process for the production of abiraterone acetate by acetylation of abiraterone in the absence of bases or acetylation catalysts.

14 Claims, 5 Drawing Sheets

PROCEDURE FOR THE PREPARATION OF ABIRATERONE ACETATE AND INTERMEDIATES THEREOF

This application is a U.S. national stage of PCT/IB2015/050613 filed on 27 Jan. 2015, which claims priority to and the benefit of Italian Application No. MI2014A000111 filed on 28 Jan. 2014, the contents of which are incorporated herein by reference in their entireties.

The present invention relates to a process for the preparation of abiraterone and abiraterone acetate with high yields and purity. A key element of the process is the isolation of a crystalline intermediate that makes the process particularly suitable for implementation on an industrial scale.

BACKGROUND TO THE INVENTION

Abiraterone acetate, the chemical name of which is (3β)-17-(3-pyridinyl)androsta-5,16-dien-3-yl acetate of formula (1), is the prodrug of the active metabolite abiraterone (2), a selective inhibitor of enzyme CYP17.

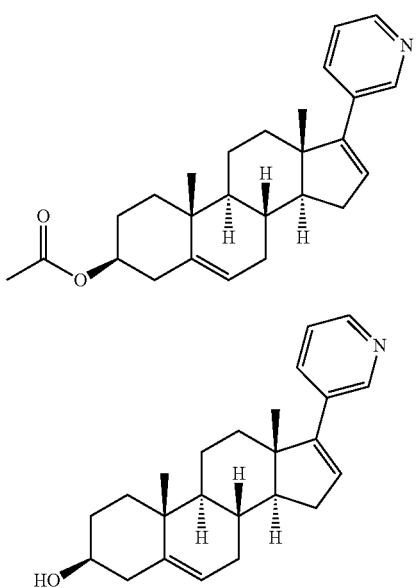

Abiraterone acetate forms the basis of the novel medicament Zytiga®, a tablet formulation containing 250 mg of active ingredient, which is administered orally at a single daily dose. When combined with prednisone or prednisolone it is indicated for the treatment of metastatic, castration-resistant prostate cancer in adult males in whom the disorder appears during or after a chemotherapy regimen based on docetaxel.

Numerous processes are reported in the literature for the preparation of abiraterone or derivatives thereof. In most cases the starting product is prasterone (dehydroepiandrosterone).

The preparation of abiraterone acetate was originally disclosed in EP0633893. Its synthesis involves conversion of the carbonyl at the 17 position of dehydroepiandrosterone-3-acetate (prasterone acetate, 3) to the corresponding enol triflate (4) by treatment with trifluoromethanesulphonic anhydride and 2,6-di-tert-butyl-4-methylpyridine (Scheme 1).

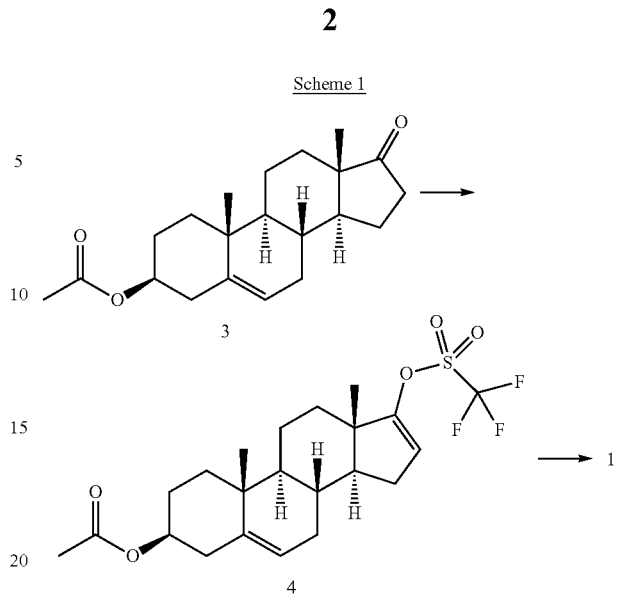

Scheme 1

The triflate intermediate is purified by chromatography on silica and then precipitated by crystallisation from hexane. The pyridine ring is introduced by Suzuki reaction between said triflate and diethyl(3-pyridyl)borane to obtain crude abiraterone acetate (1), which is purified by chromatography on silica, eluting with a mixture of ethyl ether and petroleum ether, and finally crystallised from hexane.

The use of bases which are more common and cheaper than 2,6-di-tert-butyl-4-methylpyridine is claimed in patent application WO2006/021777. The use of said bases also limits the formation of an impurity deriving from the elimination of the ester group at the 3 position, although the formation reaction of intermediate (4) is incomplete, and the crude abiraterone acetate obtained after the Suzuki reaction contains appreciable amounts of dehydroepiandrosterone-3-acetate (3). Said crude product can be purified by salification of (1) with acids, in particular with methanesulphonic acid, in tert-butyl methyl ether, as claimed in WO2006/021776; however, the purity of the methanesulphonate salt thus obtained is not very high, even after recrystallisation from isopropyl alcohol (purity of crude product <90%, purity of purified product about 96%), and yields are globally modest. Similar purifications by salification have formed the object of publications and/or patent applications, e.g. via sulphate (IPCOM000211139D), phosphate (CN102731605), oxalate (CN103059090) or trifluoroacetate (WO2013/123878).

Patent application WO2013/053691 claims the preparation of abiraterone (2) using, instead of prasterone acetate (3), the corresponding formate (5). Similarly to the sequence described above for (3), formate (5) is converted to triflate (6) and then to abiraterone formate (7), which is hydrolysed under basic conditions to obtain abiraterone (2). The latter can then be acetylated to abiraterone acetate (1) (Scheme 2).

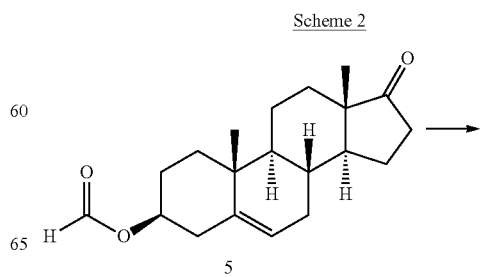

Scheme 2

-continued

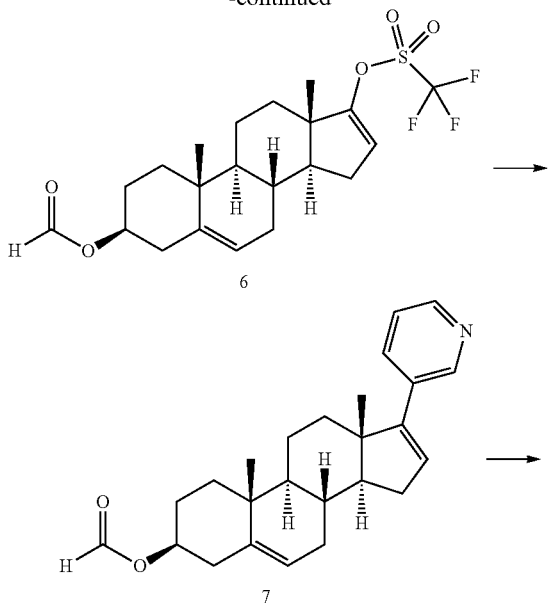

An alternative process for the preparation of abiraterone acetate is disclosed in EP0721461 (Scheme 3).

Scheme 3

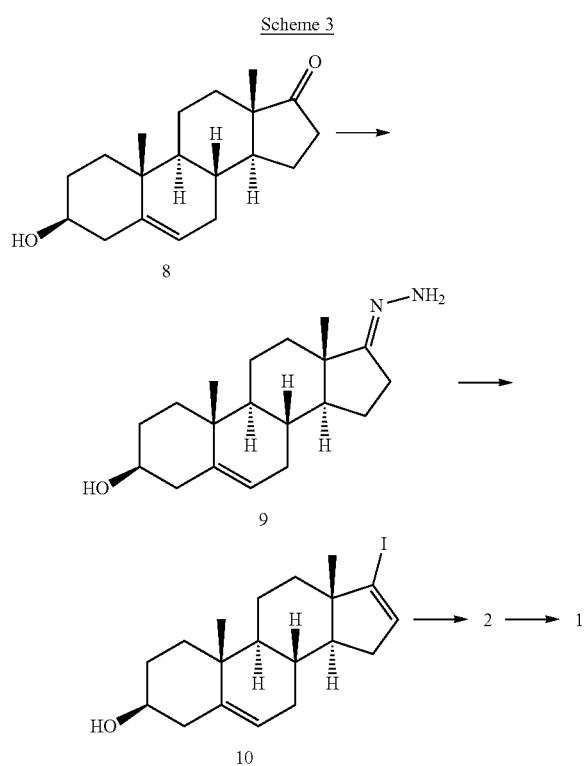

The key intermediate of said process is 17-iodo-androsta-5,16-dien-3β-ol (10), obtained in two steps from dehydroepiandrosterone (prasterone, 8) through hydrazone (9). The Suzuki reaction between vinyl iodide (10) and diethyl(3-pyridyl)borane leads to the formation of abiraterone (2), which is then acetylated to give abiraterone acetate (1).

Evaluation of the methods used to synthesise abiraterone (2) and abiraterone acetate (1) as described in the prior art demonstrates that none of said methods seem to have optimum characteristics in terms of yield, purity, workability, cost, and implementability on an industrial scale.

In many cases, impurities are formed which are difficult to remove, such as those listed below; triene (11) and the 3,5-cyclo derivative (12) are specific to synthesis via triflate, and due to impurities that accompany triflates (4) and (6), which are typically used as crude products instead of carrying out expensive chromatographic purifications on silica.

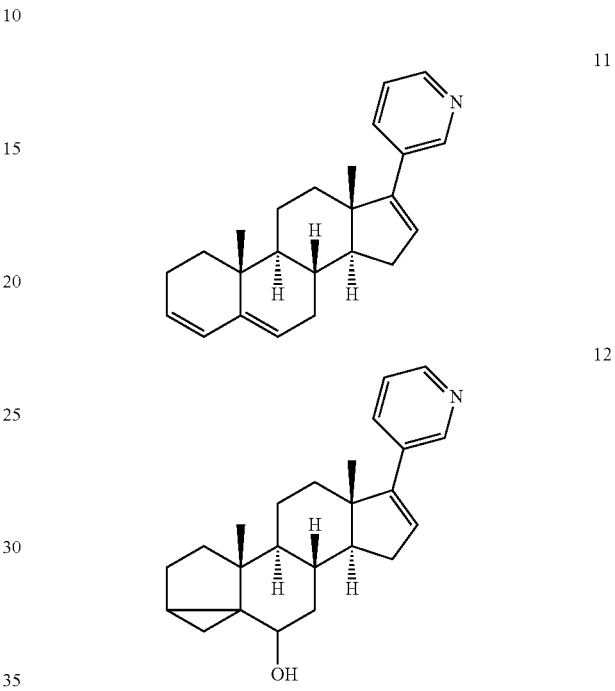

Moreover, the limited stability of said crude triflates 4 and 6 or the solutions thereof strongly influences the possibility of storage, and has an adverse impact on the planning and output of the manufacturing facility.

Preparation of abiraterone acetate (1) can also require an acetylation step, which is necessary in cases wherein the synthesis uses abiraterone (2) as precursor, such as in WO2013/053691 and WO95/09178, and also in syntheses that use prasterone acetate (3) as starting material, for example as reported in IPCOM000211139D. The acetylation processes described are unsatisfactory in terms of the complexity of the operations and/or the yields.

When the purification methods described in the prior art are used, it is very difficult to eliminate the impurities present completely; moreover the procedures are laborious, and losses are very high.

The discovery of a process that obviates the drawbacks illustrated above would therefore be highly desirable.

DESCRIPTION OF THE INVENTION

Figure 1:
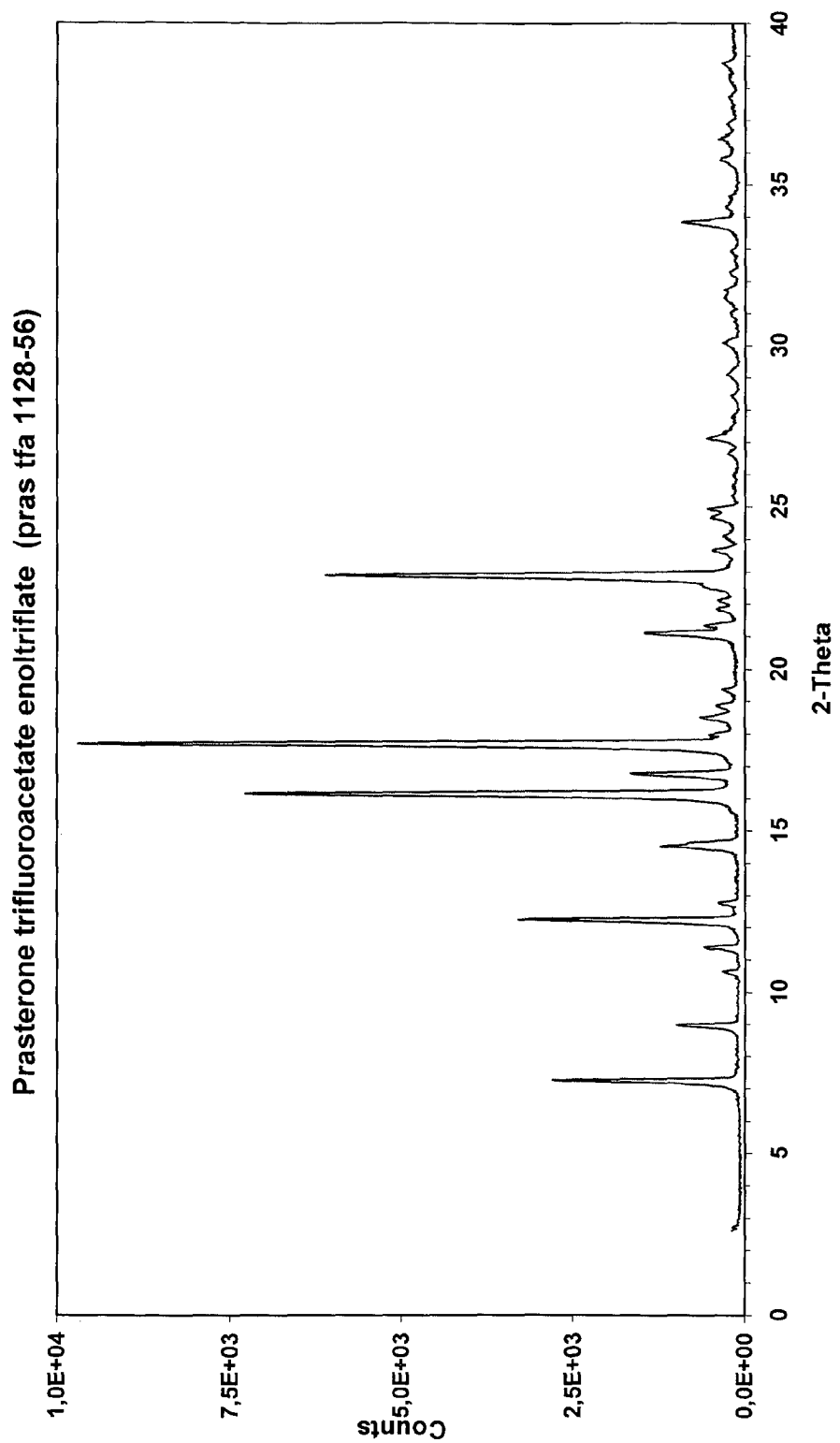
FIG. 1: X-ray powder diffraction spectrum of (14)

We have unexpectedly found that abiraterone (2) can be obtained with high yields and purity by a simple, efficient process which is easily implementable on an industrial scale, involving protecting the hydroxyl at the 3 position of prasterone as trifluoroacetate. We have also found that a key intermediate of the synthesis can be conveniently isolated as a crystalline solid. Finally, we have identified a novel method of acetylating abiraterone (2) to abiraterone acetate (1) which eliminates the limitations of the acetylation methods previously described.

The object of the present invention is therefore a process for the preparation of abiraterone (2) or abiraterone acetate (1) which comprises the following steps (Scheme 4):

Scheme 4

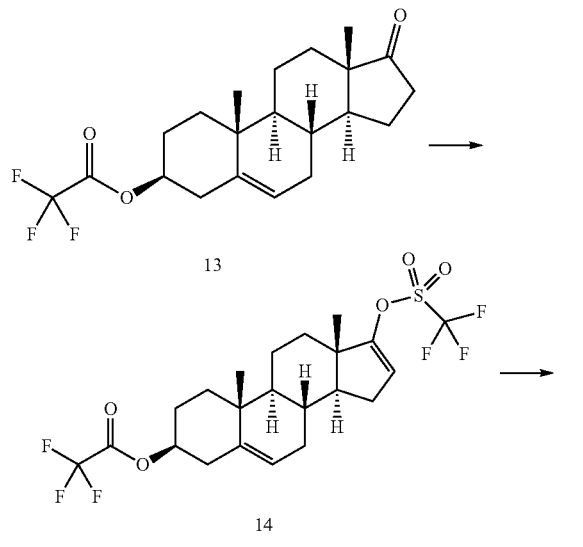

a) conversion of prasterone trifluoroacetate (13) to triflate (14)
b) optional crystallisation of triflate (14)
c) conversion of triflate (14) to abiraterone (2)
d) optional conversion of abiraterone (2) to abiraterone acetate (1).

Another object of the invention is a process for the preparation of abiraterone acetate (1) comprising acetylation of abiraterone (2) with acetic anhydride in the absence of bases or acetylation catalysts.

The compound of formula (14) is novel, and represents a further object of the invention.

DETAILED DESCRIPTION OF THE INVENTION a) Conversion of Prasterone Trifluoroacetate (13) to Triflate (14)

The triflation reaction is conducted according to known techniques for the conversion of a ketone function to a vinyl triflate. Said methods are well known to the skilled person, and have numerous applications in the field of steroids.

Operationally, the triflation reaction is typically conducted in the presence of a triflating agent and a base in an organic solvent.

The preferred triflating agents include trifluoromethanesulphonic anhydride or an imide such as N-(2-pyridyl) triflimide or N-phenyltriflimide.

The preferred bases are aromatic tertiary amines such as pyridine, picoline, lutidine, 4-dimethylamine pyridine, 2,6-di-tert-butylpyridine, 2,6-di-tert-butyl-4-methylpyridine, or aliphatic tertiary amines such as triethylamine, N-methylpyrrolidine, N-methylmorpholine, 1,4-diazabicyclo[2.2.2]octane, or inorganic bases such as alkaline metal or alkaline earth carbonates.

The preferred solvents are hydrocarbons, more preferably halogenated hydrocarbons such as methylene chloride, 1,1-dicloroethane, 1,2-dicloroethane and chlorobutane.

The reaction is conducted at a temperature ranging between −70° C. and +30° C., preferably between −30° C. and +20° C., for a reaction time ranging between 1 and 20 h, preferably between 3 and 10 h.

The conversion is typically greater than 90% and the molar yield is greater than 80%.

At the end of the reaction the reaction mixture is quenched, preferably with water or with acidic or basic aqueous solutions. The organic phase can be used directly, "as is" or after concentration, for the next step, or triflate (14) can be isolated by crystallisation as described below.

Particularly preferred conditions for the triflation reaction are as follows:
 triflating agent: trifluoromethanesulphonic anhydride (equivalents: 1.0 to 1.5)
 base: picoline (equivalents: 0.75 to 1.5)
 solvent: methylene chloride To minimise the formation of impurities, the base is conveniently added to the reaction mixture, typically in a time ranging between 1 and 5 hours, after the addition of anhydride. When operating under these conditions it is possible to have both an optimum conversion of prasterone trifluoroacetate (13) and a triflate intermediate (14) of high purity. Lowering the reaction temperature reduces the formation of impurities.

b) Optional Crystallisation of Triflate (14)

The low impurity profile of the organic phase containing triflate (14) enables it to be isolated by crystallisation. After the concentration of the organic phase, it can be crystallised by adding an organic solvent, preferably an alcohol such as methanol, or a mixture of solvents. The product thus obtained usually has a purity exceeding 90%, and the main impurity is prasterone trifluoroacetate (13).

Optionally, triflate (14) is recrystallised from alcoholic solvents, preferably from methanol. The product is obtained with good yields and very high purity (purity about 99.5%).

Triflate (14) is a crystalline product characterised by the X-ray powder diffraction (XRPD) profile, IR spectrum and 1H-NMR, 13C-NMR and 19F-NMR spectra shown in example 9.

c) Conversion of Triflate (14) to Abiraterone (2)

Triflate (14) is preferably converted to abiraterone (2) under conditions specified for a Suzuki-Miyaura condensation, also known as the Suzuki reaction and well-known to the skilled person. Triflate (14) is condensed with a 3-pyridylborane or 3-pyridylboronic derivative in the presence of a palladium-based catalyst.

The reaction solvent comprises a mixture consisting of an organic solvent, preferably tetrahydrofuran, dioxane, methyltetrahydrofuran, acetonitrile or toluene, and an aqueous solution containing an alkali bicarbonate, carbonate, hydroxide or carboxylate, such as potassium carbonate, sodium carbonate, caesium carbonate or potassium acetate.

The 3-pyridyl borane derivative is preferably a dialkyl(3-pyridyl)borane.

The 3-pyridylboronic derivative is preferably 3-pyridylboronic acid or an ester thereof. The use of diethyl(3-pyridyl)borane is particularly preferred.

The catalyst is preferably tetrakis triphenylphosphine palladium, bis(triphenylphosphine)palladium dichloride, or palladium acetate or palladium chloride, in the presence of a ligand such as triphenylphosphine.

The reaction is typically conducted hot, at a temperature ranging between 40° C. and the reflux temperature of the mixture.

Suitable reaction conditions are, for example, those described in the patents/patent applications cited above for triflate (4).

A preferred procedure involves reacting triflate (14), isolated or unisolated, crude or purified, with diethyl(3-pyridyl)borane in the presence of bis(triphenylphosphine) palladium dichloride in a mixture comprising an organic solvent such as tetrahydrofuran, acetonitrile or methyltetrahydrofuran, and an aqueous solution of an alkaline carbonate.

Preferably, about 1.0 to 1.5 equivalents of diethyl(3-pyridyl)borane and 2 to 10 equivalents of sodium or potassium carbonate per mole of triflate (14) are added to the reaction mixture. More preferably, about 1.1 to 1.3 equivalents of diethyl(3-pyridyl)borane and 3 to 5.5 equivalents of sodium or potassium carbonate per mole of triflate (14) are added to the reaction mixture.

Evaluation of the stoichiometric ratio, which is difficult to conduct when the triflates are not isolatable or not isolated, as in the case of triflate (3) or (5), is particularly convenient with triflate (14), which is isolatable as a crystalline solid, the assay value of which can easily be determined. It is therefore possible to measure the borane derivative accurately, with benefits in terms of quality and yield of the reaction product.

The catalyst is preferably added in quantities ranging from 0.001 to 0.020 triflate (14) equivalents.

The reaction is preferably conducted at reflux temperature, and the reaction and hydrolysis time ranges from 1 to 6 hours, preferably 2 to 4 hours.

The product of the reaction is abiraterone (2). The typical conditions of the Suzuki reaction applied to triflate (14) cause simultaneous hydrolysis of trifluoroacetate at the 3 position of the steroid. Typically, abiraterone (2) precipitates from the reaction mixture and can be recovered, optionally after the addition of water to the reaction mixture and/or partial concentration of the mixture, by simple filtration.

The abiraterone (2) thus obtained is characterised by a high degree of purity, typically exceeding 98%. If necessary it can be recrystallised from an organic solvent such as methanol, ethanol, isopropanol, acetonitrile, tetrahydrofuran, methyltetrahydrofuran, ethyl acetate, isopropyl acetate or methylene chloride, or a mixture thereof. The product is obtained with good yields and very high purity (>99.5%).

Abiraterone (2) can then be converted to abiraterone acetate (1) by one of the known methods. The acetylation can be conducted, for example, with an acetylating agent such as acetyl chloride or acetic anhydride in the presence of an organic base such as pyridine or triethylamine. However, we have found that said conditions are unsatisfactory to obtain abiraterone acetate (1) with high yields and purity, and above all the operations involving recovery of the reaction product and elimination of the organic base (or salts thereof) used as acid acceptor in the reaction are laborious. This complication will be understood if it is borne in mind that abiraterone and the corresponding acetate are structurally characterised by the presence of a pyridine group.

We have unexpectedly found that abiraterone (2) can be acetylated to abiraterone acetate (1) in the absence of bases or acetylation catalysts, simply by treating abiraterone (2) hot with acetic anhydride.

The typical reaction conditions are as follows:
Reagent: 1.5 to 20 acetic anhydride equivalents per mole of abiraterone. More preferably, about 10 to 15 acetic anhydride equivalents.
Solvent: without solvent or in aprotic solvent, for example an ester such as ethyl acetate, methyl acetate, isopropyl acetate or butyl acetate.
Temperature: 20° C. to 85° C., preferably 50° C. to 75° C.
Time: 1 to 20 hours.
End of reaction: reaction suitably monitored by HPLC; conversion typically >99.5%.
Work-up: The amount of acetic anhydride present at the end of the reaction can be conveniently eliminated or drastically reduced by treating the reaction mixture hot with water or an alcohol, preferably a primary alcohol such as methanol.

The resulting mixture is then treated one or more times with an aqueous solution of an alkaline carbonate or bicarbonate to remove the acetic acid formed during the reaction, and any traces of acetic anhydride. The organic phase can then be treated with decolourising carbon and suitable chelating resins.

Isolation: abiraterone acetate (1) can be isolated by simple filtration of the concentrated solution, or the residue after concentration can be crystallised from an organic solvent or mixture of solvents, preferably selected from acetonitrile, methanol, ethanol and isopropyl alcohol.

The purity of the abiraterone acetate (1) thus obtained is greater than 99.5%, typically ≥99.8%.

Prasterone trifluoroacetate (13) is a known product which can be prepared by known techniques from prasterone (dehydroepiandrosterone) (8), a commercially available intermediate that is widely used in the production of steroid derivatives.

The invention will now be illustrated by the following examples.

Example 1

Synthesis of Prasterone Trifluoroacetate Triflate

Trifluoromethanesulphonic anhydride (47 mL) and a solution of picoline (26 mL) in methylene chloride (200 mL) are added in sequence to a solution of prasterone trifluoroacetate (100 g) in methylene chloride (1.8 L), maintaining the temperature at −25° C. (±5° C.), and left under stirring for about 9 h. After the addition of water (1.5 L), the organic phase is separated and washed with water and aqueous sodium chloride, concentrated under vacuum and methanol (about 400 mL) is added, to obtain a precipitate. The solid is filtered, washed with methanol and dried under vacuum. The crude triflate thus obtained (about 130 g; HPLC analysis indicates a content of 118 g of pure triflate and 9.6 g of prasterone trifluoroacetate) can be used to prepare abiraterone without further purification.

Example 2

Synthesis of Abiraterone

In an inert gas environment, diethyl(3-pyridyl)borane (28 g), bis(triphenylphosphine)palladium dichloride (1.2 g) and a 2M aqueous solution of sodium carbonate (320 mL) are added to a solution of prasterone trifluoroacetate triflate prepared as described in example 1 (100 g) in tetrahydrofuran (1.4 L). The resulting mixture is refluxed for about 2 h; it is then cooled to room temperature and water (1.0 L) is added. The suspension is cooled to 0-5° C. and filtered. After drying, 42 g of crude abiraterone is obtained (purity about 98%).

Example 3

Synthesis of Abiraterone Acetate

Acetic anhydride (438 g) is added to a suspension of abiraterone (100 g) in ethyl acetate (600 mL). The solution is refluxed until the reaction is complete (about 10 h); the temperature is then reduced to about 50° C. and methanol (230 mL) is added. The solution is maintained under stirring for 2 h, then cooled to ambient temperature, and ethyl acetate (400 mL) and an aqueous solution of sodium carbonate (1.2 L) are added. The phases are separated and the organic phase is treated with decolourising carbon. After concentration under vacuum, the concentrate is taken up with acetonitrile (about 500 mL) to obtain a sandy solid, which is isolated by filtration at 0-5° C. and dried under vacuum at 40° C. for 16 h (about 80 g; purity: 99.8%).

Example 4

Synthesis of Abiraterone Acetate

A suspension of abiraterone (50 g) in acetic anhydride (220 g) is heated to 70° C. until the reaction is complete (about 8 h); it is then cooled to 50° C. (±5° C.) and methanol (150 mL) is added. The mixture is maintained under stirring at 50° C. for 2 h, then cooled to room temperature. Ethyl acetate (350 mL) and an aqueous solution of sodium bicarbonate (300 mL) are added. The phases are separated and the organic phase is treated with decolourising carbon, then concentrated under vacuum and the concentrate is taken up with acetonitrile (about 250 mL) to obtain a sandy solid, which is isolated by filtration and dried under vacuum (about 50 g; purity: 99.8%).

Example 5

Synthesis of Abiraterone

In an inert gas environment, diethyl(3-pyridyl)borane (6.9 g), bis(triphenylphosphine) palladium dichloride (0.3 g) and a 2M aqueous solution of sodium carbonate (106 mL) are added to a solution of prasterone trifluoroacetate triflate prepared as described in example 1 (25 g) in tetrahydrofuran (350 mL). The resulting mixture is refluxed for about 2 h; it is then cooled to room temperature and water (250 mL) is added. The suspension is concentrated under vacuum to half its volume, and then filtered. 13 g of crude abiraterone is obtained (purity about 90%).

Example 6

Synthesis of Abiraterone Acetate

Abiraterone obtained as described in example 5 is acetylated by the procedure described in example 3. The abiraterone acetate thus obtained is purified by crystallisation from acetonitrile (yield 93% w/w; purity >99.5%).

Example 7

Synthesis of Prasterone Trifluoroacetate Triflate

The preparation described in example 1 is conducted at the temperature of 0° C. (±5° C.) for about 6 h. After the addition of water, the organic phase is separated and washed with water and aqueous sodium chloride. The solution is concentrated under vacuum and methanol and acetonitrile are added to obtain a precipitate, which is isolated by filtration and dried under vacuum. The titular product is obtained with a yield of 115% w/w and 97% purity.

A product with 99.5% purity is obtained by recrystallisation from methanol.

Example 8

Synthesis of Prasterone Trifluoroacetate Triflate

Trifluoromethanesulphonic anhydride (25 mL) at −10° C. (±5° C.), and sodium carbonate (35 g) in portions, are added in sequence to a solution of prasterone trifluoroacetate (50 g) in methylene chloride (0.8 Lt). The solution is maintained under stirring for about 12 h, and water is then added. The organic phase is separated and washed with water and aqueous sodium chloride. The solution is concentrated under vacuum and methanol is added, followed by acetonitrile (methanol/acetonitrile ratio 2:1; about 300 mL) to obtain a precipitate. The solid is filtered, washed with methanol and dried under vacuum (about 60 g, purity >98%).

Example 9

Characterisation of Prasterone Trifluoroacetate Triflate

Prasterone trifluoroacetate triflate is a crystalline product characterised by the X-ray powder diffraction (XRPD) profile, IR spectrum and $^1$H-NMR, $^{13}$C-NMR and $^{19}$F-NMR spectra reported below.

XRPD

The XRPD diffractogram was obtained with the instrumentation and under the conditions described below:
Diffractometer: Bruker D2
Goniometer: theta/theta
Radiation: CuKα (λ=1.5419 Å)
Detector: 1-dimensional LYNXEYE
Scanning: continuous
Voltage: KV 30, mA 10
Scanning interval: 2.6-40° 2θ
Increment: 0.02° 2θ
Time per increment: 53 sec The XRPD spectrum is substantially as shown in FIG. 1, and comprises the peaks, at 2-theta (2θ) angle values, reported in Table 1.

TABLE 1

| Angle (2θ) | Intensity (count) | Relative Intensity (%) |
|---|---|---|
| 7.26 | 2795 | 28.80 |
| 8.99 | 1003 | 10.33 |
| 10.65 | 335 | 3.45 |
| 11.40 | 594 | 6.12 |
| 12.25 | 3297 | 33.97 |
| 12.78 | 390 | 4.02 |
| 14.53 | 1239 | 12.77 |
| 16.15 | 7286 | 75.07 |
| 16.78 | 1666 | 17.17 |
| 17.71 | 9705 | 100.00 |
| 18.52 | 650 | 6.70 |
| 21.12 | 1457 | 15.01 |
| 21.34 | 594 | 6.12 |
| 22.90 | 6112 | 62.98 |
| 24.95 | 552 | 5.69 |
| 27.12 | 559 | 5.76 |
| 33.83 | 929 | 9.57 |

IR

Figure 2:
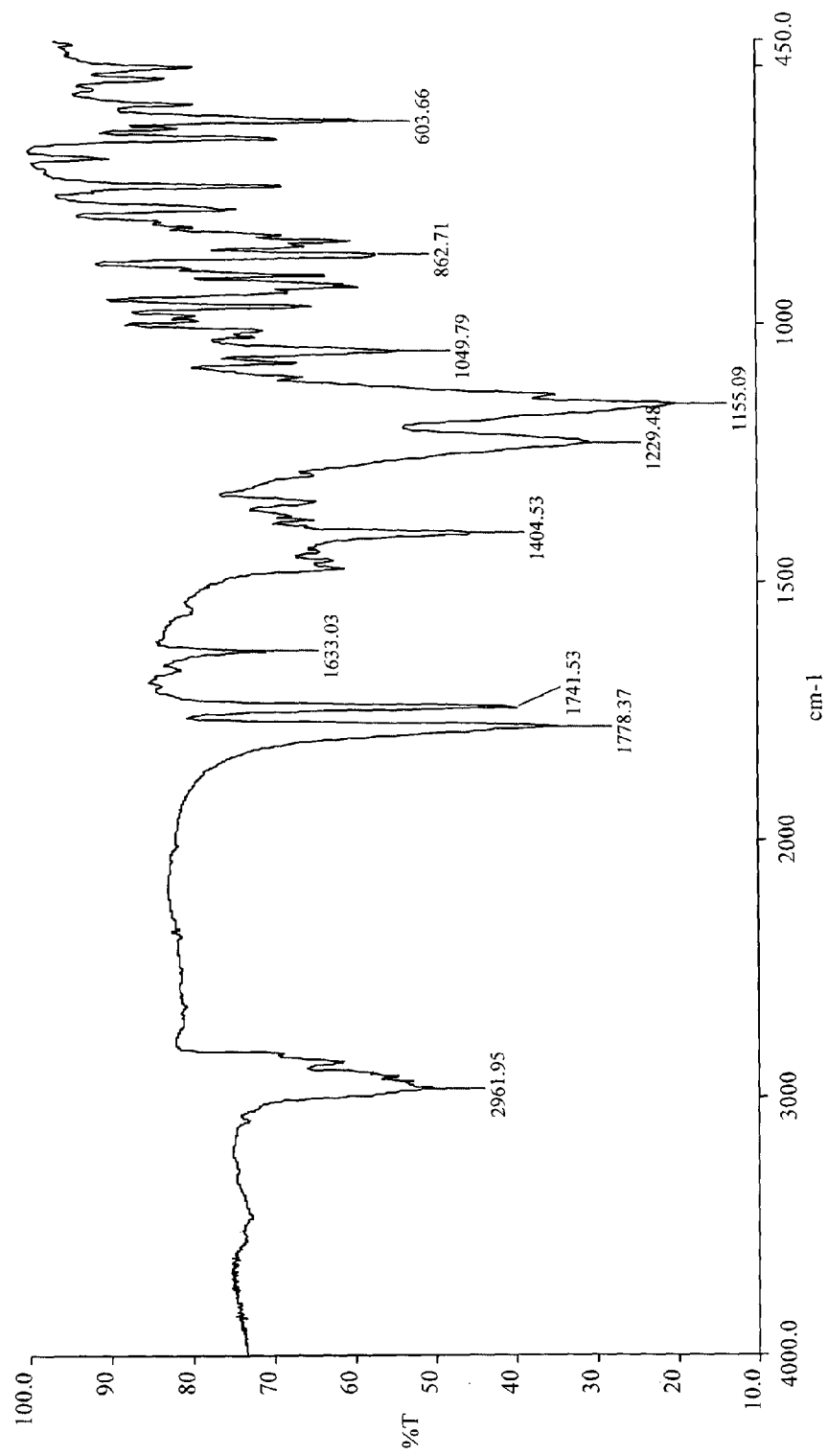
FIG. 2: Infrared spectrum of (14)

The IR spectrum (1% KBr pellet) was acquired in transmittance mode using a Perkin Elmer Spectrum 1000 spectrophotometer, and is reported in FIG. 2. It comprises characteristic absorption bands at 2962, 1778, 1741, 1633, 1229 and 1155 cm$^{-1}$, inter alia.

NMR

The NMR spectra were acquired with a Varian Mercury 300 spectrometer using deuterated chloroform as solvent.

Figure 3:
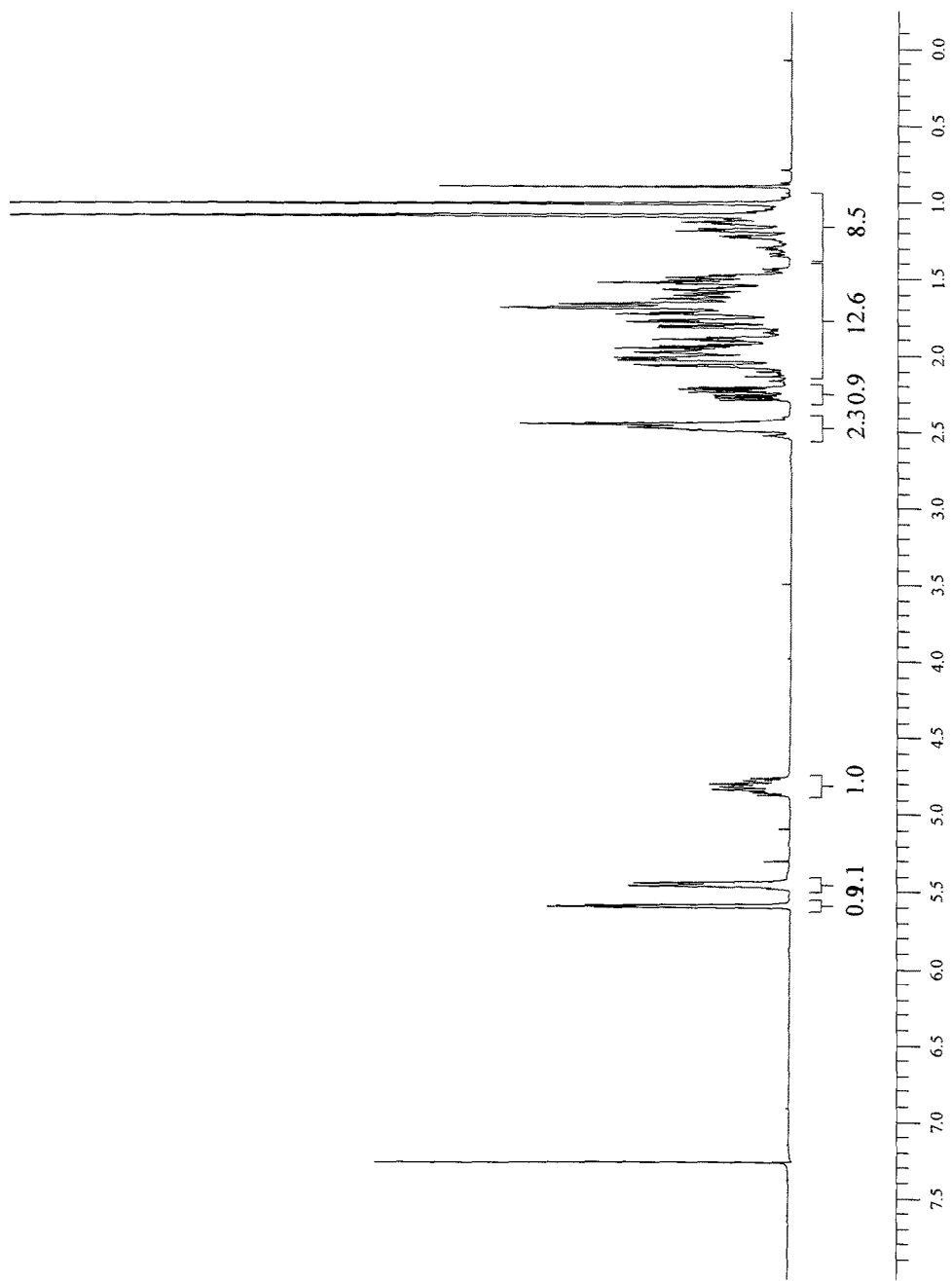
FIG. 3: $^1$H-NMR spectrum of (14)

The $^1$H-NMR spectrum is reported in FIG. 3, and shows (inter alia) the following chemical shifts δ (ppm): 5.59, m, 1H; 5.44, d, J=5.5 Hz, 1H; 4.81, m, 1H; 1.0-2.5, m, steroid ring; 1.00, 1.08, s, 2CH$_3$.

Figure 4:
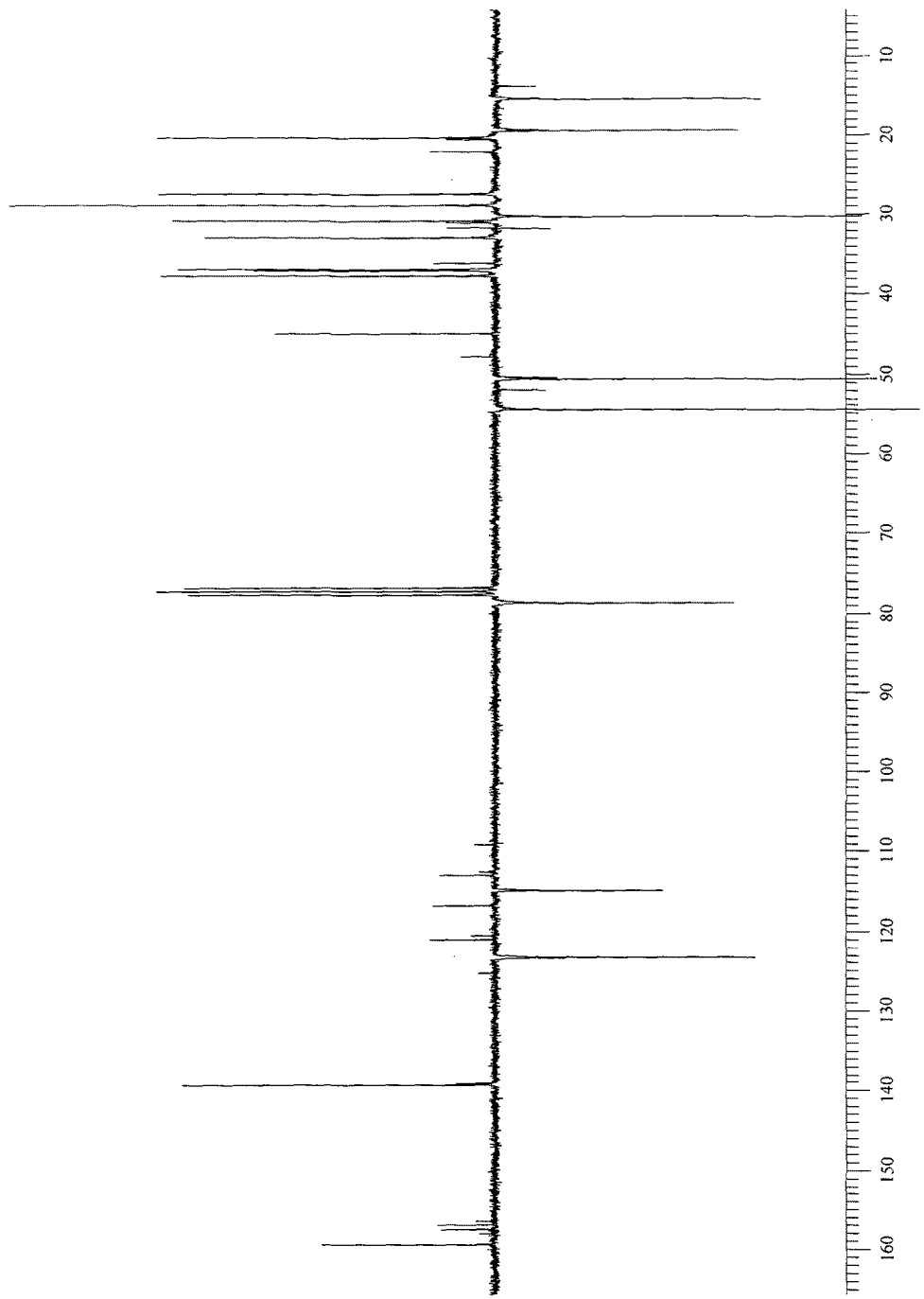
FIG. 4: $^{13}$C-NMR spectrum of (14)

The $^{13}$C-NMR spectrum (Attached Proton Test) is reported in FIG. 4, and shows (inter alia) the following chemical shifts δ (ppm): 159, 139, 2=C; 123.1, 114.6, 2=CH—; 157, 118, 2 CF$_3$; 78.7, O—CH.

Figure 5:
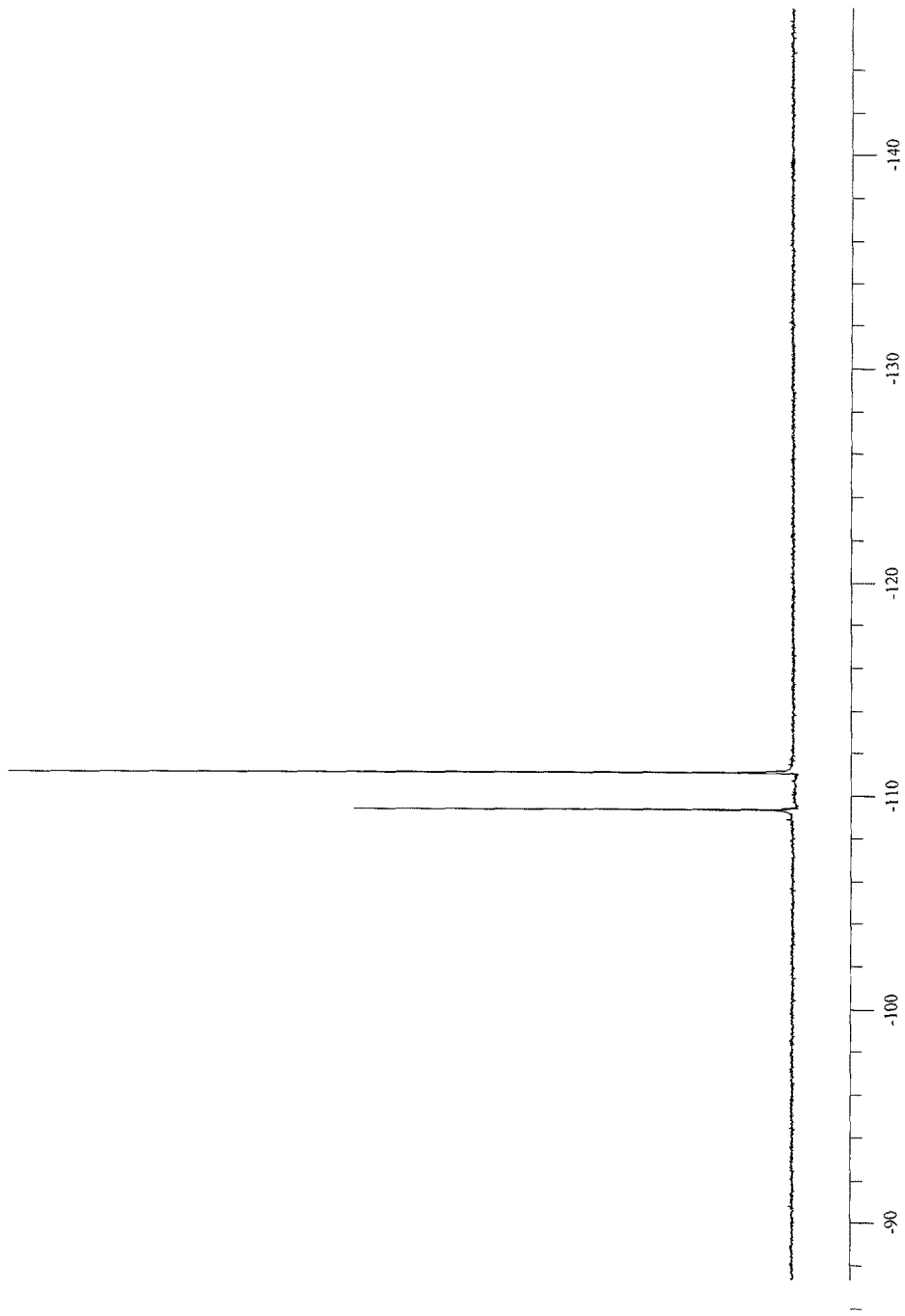
FIG. 5: $^{19}$F-NMR spectrum of (14)

The $^{19}$F-NMR spectrum is reported in FIG. 5, and shows the following chemical shifts δ (ppm): 109, 111, 2 CF$_3$.

The invention claimed is:

1. Process for the preparation of abiraterone (2) or abiraterone acetate (1)

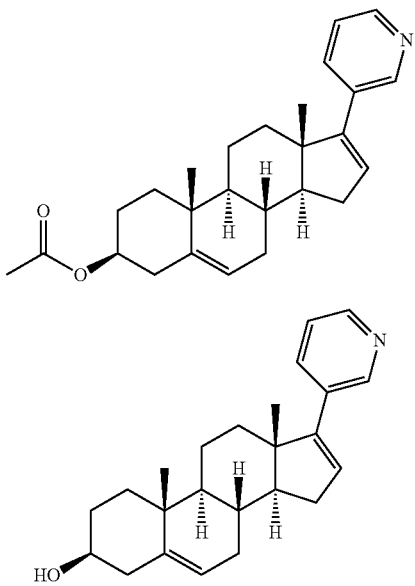

which comprises the following steps:
a) converting prasterone trifluoroacetate (13)

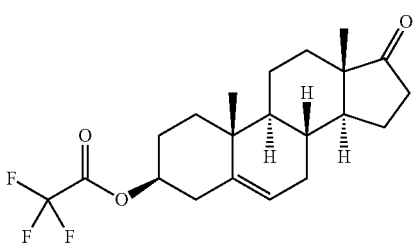

to the triflate (14)

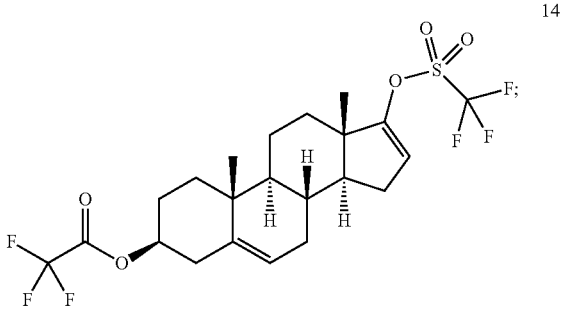

b) optional crystallizing (14);
c) converting (14) to abiraterone (2);
d) optional converting abiraterone (2) to abiraterone acetate (1).

2. Process for the preparation of abiraterone (2) according to claim 1.

3. Process according to claim 2 wherein step a) is carried out in the presence of a triflating agent anhydride, and of a base selected from the group consisting of aromatic or aliphatic tertiary amines or inorganic bases in an organic solvent.

4. Process according to claim 2 wherein the optional crystallizing of (14) takes place in an alcoholic solvent.

5. Process according to claim 2 wherein (14) is condensed in step c) with a 3-pyridylborane or 3-pyridylboronic derivative in the presence of a palladium-based catalyst in a reaction solvent comprising a mixture consisting of an organic solvent and an aqueous solution containing an alkali bicarbonate, carbonate, hydroxide or carboxylate.

6. Process according to claim 1 for the preparation of abiraterone acetate (1).

7. Process according to claim 6 wherein step d) comprises the reaction of abiraterone (2) with acetic anhydride in the absence of bases or acetylation catalysts.

8. Process according to claim 7 wherein step d) is carried out without solvent.

9. Process according to claim 7 wherein step d) is carried out in an aprotic solvent.

10. Process according to claim 9 wherein the aprotic solvent is an ester selected from ethyl acetate, methyl acetate, isopropyl acetate and butyl acetate.

11. Process for the preparation of abiraterone acetate (1) comprising the acetylation of abiraterone (2) with acetic anhydride in the absence of bases or acetylation catalysts.

12. Process according to claim 11 wherein the acetylation of abiraterone (2) is carried out in the absence of solvent.

13. Process according to claim 12 wherein the acetylation of abiraterone (2) is carried out in an aprotic solvent.

14. Process according to claim 13 wherein the aprotic solvent is an ester selected from ethyl acetate, methyl acetate, isopropyl acetate and butyl acetate.

* * * * *